US006703369B1

(12) United States Patent
de Smidt et al.

(10) Patent No.: US 6,703,369 B1
(45) Date of Patent: Mar. 9, 2004

(54) LIPASE INHIBITING COMPOSITIONS

(75) Inventors: Passchier Christiaan de Smidt, Pamplona (ES); Paul Hadvary, Biel-Benken (CH); Hans Lengsfeld, Basel (CH); Marcel Schmid, Reinach (CH); Donald MacFarland Small, Quincy, MA (US); Hans Steffen, Liestal (CH); Joseph Tardio, St. Louis (FR)

(73) Assignee: Hoffman-La Roche Inc., Nutley, NJ (US)

( * ) Notice: Subject to any disclaimer, the term of this patent is extended or adjusted under 35 U.S.C. 154(b) by 93 days.

(21) Appl. No.: 09/660,700

(22) Filed: Sep. 13, 2000

(30) Foreign Application Priority Data

Sep. 13, 1999 (EP) .............................. 99118179

(51) Int. Cl.[7] .................. A61K 31/70; A61K 31/335
(52) U.S. Cl. .................. 514/23; 514/449; 514/547
(58) Field of Search ................ 514/449, 547, 514/23

(56) References Cited

U.S. PATENT DOCUMENTS

| 4,598,089 A | 7/1986 | Hadvary et al. |
| 5,741,496 A | 4/1998 | Khaiat |
| 6,004,996 A | 12/1999 | Shah et al. |

FOREIGN PATENT DOCUMENTS

| WO | WO 98/34607 | 8/1998 |
| WO | WO 98/34630 | 8/1998 |
| WO | WO 99/34786 | 7/1999 |
| WO | WO 00/09122 | 2/2000 |
| WO | WO 00/09123 | 4/2000 |

OTHER PUBLICATIONS

Merck Index, 12, (1996), p. 1657.

Primary Examiner—Zohreh Fay
(74) Attorney, Agent, or Firm—George W. Johnston; John P. Parise

(57) ABSTRACT

A pharmaceutical composition contains at least one inhibitor of lipases and at least one fatty acid ester of polyol. In this composition, the fatty acid ester has a melting point above the body temperature and the polyols are chosen from the group consisting of sugars, sugar derivatives, and mixtures thereof.

22 Claims, No Drawings

LIPASE INHIBITING COMPOSITIONS

BACKGROUND OF THE INVENTION

1. Field

The present invention relates to pharmaceutical compositions comprising at least one lipase inhibitor.

2. Description

Lipase inhibitors include lipstatin and orlistat. The latter is also known as tetrahydrolipstatin or THL and is derived from a natural product excreted by *Streptomyces toxytricini*. This class of compounds was found to exhibit in vitro as well as in vivo activity against various lipases, such as lingual lipase, pancreatic lipase, gastric lipase, and carboxylester lipase. Its use for the control or prevention of obesity and hyperlipidemia is described, for instance, in U.S. Pat. No. 4,598,089.

Orlistat is currently administered at doses of 120 mg per meal and dosing is independent of the body mass of the human subject. Orlistat acts locally in the gastrointestinal (GI) tract and prevents lipase from digesting triglycerides and subsequently inhibits the formation of absorbable lipid degradation products. For this reason, systemic availability of the lipase inhibitors is not required; instead, local residence in the gastrointestinal tract is preferred.

Lipase inhibitor compositions currently administered inhibit around 30% of fat absorption after consumption of a mixed meal; an increase of the lipase inhibitors concentration in the pharmaceutical composition does not increase its clinical efficacy and/or potency while the intensity of local side effects increases.

Anal leakage of oil (oily spotting) is an adverse effect occasionally observed in patients treated with lipase inhibitors. This phenomenon reflects the physical separation of liquid unabsorbed dietary fat from the bulk of solids in the lower large intestine.

There has been a long felt need for a solution to the problem of providing lipase inhibitor compositions that improve clinical efficacy and/or potency of the inhibitor itself and/or minimize or suppress the above-mentioned disadvantages. The present invention addresses this need.

SUMMARY OF THE INVENTION

The subject invention provides a pharmaceutical composition comprising at least one lipase inhibitor and at least one fatty acid ester of a polyol. The fatty acid ester of a polyol has a melting point above body temperature and the polyol is chosen from the group consisting of glycerol, sugars, sugar derivatives, and mixtures of sugars and sugar derivatives. Preferably, the polyol is selected from the group consisting of sucrose, glycerol, and sugar alcohols, and is more preferably glycerol.

A favored fatty acid ester of a polyol is a glyceride ester, where the glyceride moiety is chosen from the group consisting of one or more triglycerides, one or more monoglycerides, one or more phospholipids, and mixtures thereof. The fatty acid moieties in the fatty acid ester of the polyol typically have, independently from each other, twelve or more carbon atoms, for example, twelve to twenty carbon atoms. Favorably, the fatty acid moiety in the fatty acid ester of the polyol is saturated Favored polyols are triglycerides chosen from the group consisting of trilaurin, trimyristin, tripalmitin, tristearin, and mixtures thereof, and more favorably trimyristin, trilaurin, or a mixture thereof. Preferred monoglycerides are chosen from the group consisting of monocaprin, monolaurin, monomyristin, monopalmitin, and mixtures thereof. A preferred glyceride ester is an ester of a phospholipid that is a lecithin, such as a non-, partially or fully hydrogenated lecithin, or a mixture thereof. Favored lecithins include natural lecithin, synthetic lecithin, soya lecithin, egg lecithin, synthetic dipalmitoyllecithin, partially or fully hydrogenated lecithin, and mixtures thereof.

In a preferred embodiment, the at least one fatty acid ester of a polyol is present in an amount varying between 0.5% and 90% of the total weight of the composition, and further comprises at least one pharmaceutically acceptable excipient. Excipients are generally selected from the group consisting of carbohydrates, starch, starch derivatives, maltodextrines, cellulose, celluose derivatives, sugars, fillers, disintegrants, effervescents, antioxidants, anionic surfactants, nonionic surfactants, and mixtures thereof. A favored excipient is a surfactant selected from the group consisting of sodium dodecylsulfate, fatty acid salts, polyoxyethylene alkyl esters and polyoxyethylene alkyl ethers, and mixtures thereof. Other suitable excipients are selected from the group consisting of glucose, lactose, sorbitol, maltodextrin, talcum, magnesium stearate, mannitol, sodium bicarbonate, Crospovidone, glycofurol, tartaric acid, and mixtures thereof.

A desirable lipase inhibitor is an inhibitor of a gastrointestinal lipase, such as orlistat. This lipase inhibitor is typically present in an amount between 1% and 50% of the total weight of the composition, and favorably between 5% and 30% of the total weight of the composition. Preferred compositions comprise at least one lipase inhibitor that forms from 1% to 50% of the total weight of the composition, and at least one fatty acid ester of a polyol that forms from 0.5% to 90% of the total weight of the composition. Such composition may further comprise one or more pharmaceutically acceptable excipient(s).

DETAILED DESCRIPTION OF THE PREFERRED EMBODIMENTS

The subject invention will now be described in terms of its preferred embodiments. These embodiments are set forth to aid in understanding the invention but are not to be construed as limiting.

The subject invention provides a pharmaceutical composition comprising at least one inhibitor of lipases and at least one fatty acid ester of polyols, characterized in that the fatty acid ester has a melting point above the body temperature, e.g., >37° C., and the polyols are chosen from the group consisting of glycerol, sugars, sugar derivatives, and mixtures thereof.

It has surprisingly been found that administering a lipase inhibitor in a composition comprising at least one of the above fatty acid esters improves the efficacy and potency of the lipase inhibitor itself. Furthermore, inter-subject variability in efficacy and/or potency is reduced, as is the frequency and intensity of side effects.

The pharmaceutical compositions according to the present invention have been found to exhibit very favorable effects when applied orally during meal intake in humans, including an increased efficacy and potency compared to the already known compositions. This was unexpected because the compositions according to the invention are solid within the body and therefore it was expected that they should be poorly dispersed among the dietary oil particles in the stomach.

Furthermore, the inventive compositions reduce the unpleasant side effects in the single meal test compared to known compositions, despite a greater amount of fat remaining unabsorbed. During the single meal studies with human subjects, it was observed that stools obtained after intake of compositions according to the present invention show less separation of oil from the main stool mass as compared to conventional formulations. This was unexpected because equal or higher amounts of fat were present in the collected stools.

According to the present invention, the terms "inhibitor of lipases" and "lipase inhibitor" refer to compounds that are capable of inhibiting the action of lipases, for example gastric and pancreatic lipases. Orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins, analogues of orlistat [Mutoh et al, J. Antibiot., 47(12):1369–1375 (1994)]. The term "lipase inhibitor" refers also to polymer bound lipase inhibitors for example described in International Patent Application WO99/34786 (Geltex Pharmaceuticals Inc.). These polymers are characterised in that they have been substituted with one or more groups that inhibit lipases. The term "lipase inhibitor" also includes pharmaceutically acceptable salts of these compounds. The preferred "lipase inhibitor" is orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described in International Patent Applications WO 00/09122 and WO 00/09123.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, e.g., a human with a body mass index of 25 or greater. Generally, it is preferred that the lipase inhibitor be administered during a meal containing fat. Generally, for administering a lipase inhibitor as defined above it is preferred that treatment be administered to a human who has a strong family history of obesity and has obtained a body mass index of 25 or greater.

The polyols can be chosen, independently from each other, from the group consisting of glycerol, sugars, sugar derivatives and mixtures of sugars and sugar derivatives. This group especially comprises sucrose, glycerol, and sugar alcohols, and most preferably glycerol, i.e. most preferably glyceride esters are used in the compositions according to the present invention.

The term "sugar alcohols" refer to compounds comprising mono-, oligo- and polysaccharides and their reduction products, e.g. mannitol.

The term "glyceride ester" refers to an ester of glycerol. According to the present invention, an ester may contain one to three, preferably one or three $C_{12}$ to $C_{20}$ fatty acid(s) moieties per glycerol moiety or may be a phospholipid, preferably a lecithin or mixtures thereof. For example, the glyceride esters can be chosen from the group consisting of one or more triglycerides, one or more monoglycerides, one or more phospholipids and mixtures thereof. Preferably, the fatty acid moieties in the fatty acid ester of the polyols have, independently from each other, twelve or more carbon atoms, preferably twelve to twenty carbon atoms. Most preferably, the fatty acid moieties in the fatty acid esters of the polyols hve twelve to twenty carbon atoms and are saturated.

In a preferred embodiment of the present invention suitable triglycerides are trilaurin, trimyristin, tripalmitin and tristearin and mixtures thereof. The most preferred triglycerides are trimyristin and trilaurin.

The monoglycerides can be chosen from the group consisting of monocaprin, monolaurin, monomyristin and monopalmitin and mixtures thereof.

In a preferred embodiment of the present invention, the phospholipid is preferably a lecithin, e.g. a non-, partially or fully hydrogenated lecithin or a mixture thereof. The term "lecithin" in the context of this invention refers to esters formed of glycerol, two fatty acids, and a phosphorylcholine moiety. A lecithin has the following structure:

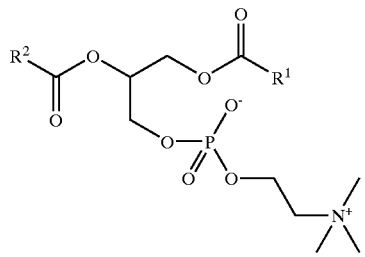

wherein $R^1$—COO— and $R^2$—COO— are moieties derived from fatty acids as defined above.

The phospholipids, e.g. lecithins, may be chosen from the group consisting of natural lecithin, synthetic lecithin, soya lecithin, egg lecithin, synthetic dipalmitoyllecithin, partially or fully hydrogenated lecithin and mixtures thereof.

The fatty acid esters of polyols are known in the art and are commercially available.

Preferably, the glyceride ester is present in an amount varying between 0.5 and 90% of the total weight of the composition.

Advantageously, the pharmaceutical compositions of the present invention further comprise at least one pharmaceutically acceptable excipient. The additional excipient may be useful for enhancing the dispersion and distribution in the stomach. The excipient may be chosen from the group consisting of disintegrants, effervescents and mixtures thereof. Further excipients such as carbohydrates, starch and/or its derivatives, maltodextrines, sugars, fillers, antioxidants, anionic and nonionic surfactants such as sodium dodecylsulfate, fatty acid salts, e.g. Na-stearate, polyoxyethylene alkyl esters, polyoxyethylene alkyl ethers and mixtures thereof can also be added. Examples of additional excipients are glucose, lactose, sorbitol, maltodextrin, talcum, magnesium stearate, mannitol, sodium bicarbonate, crospovidone, glycofurol, tartaric acid and mixtures thereof The invention is useful with any inhibitor of lipases, but is especially useful for inhibitors of the gastric and pancreatic lipase and, in particular, for the active compound orlistat.

According to the present invention, the lipase inhibitor is present in an amount varying from 1 to 50%, preferably from 5 to 30%, of the total weight of the composition.

In a preferred embodiment of the present invention the pharmaceutical composition as described above may comprise a) 1 to 50% of the total weight of the composition is a lipase inhibitor;

b) 0.5 to 90% of the total weight of the composition is at least one fatty acid ester of polyols; and optionally the composition comprises one or more pharmaceutically acceptable excipient(s).

The compositions according to the present invention can be administered using conventional dosage forms such as hydroxypropylmethylcellulose (HPMC) capsules, hard gelatin capsules, starch capsules, tablets, chewable tablets and capsules, powders, pellets, granules, etc.

The present invention relates also to a process for preparing pharmaceutical compositions as described above, which process comprises mixing at least one inhibitor of lipases with at least one fatty acid ester of polyols, in the solid or molten state, wherein the fatty acid ester of polyols has a melting point above the body temperature and the polyols are chosen from the group consisting of glycerol, sugars, sugar derivatives and mixtures thereof.

A further aspect of the present invention is to provide a method for controlling or preventing obesity comprising the step of administering to a patient a pharmaceutical composition as described above.

The invention also relates to the use a composition as defined above for the preparation of a medicament for the prevention and treatment of obesity.

The invention will be now illustrated in details by the following examples.

The efficacies on fat excretion of orlistat formulations according to examples 1–10 and of Xenical® brand of orlistat as a reference are reported in table 1.

EXAMPLES

Example 1

10 g of melted trimyristin (Dynasan 114, Hüls AG) were mixed with 20 g orlistat during about 30 minutes at a temperature of 57–63° C. 20 g glucose were added to the so obtained co-melt and mixed until solidification at room temperature. The so obtained cake was left for an hour at room temperature, ground by means of a dry mixer and subsequently sieved through meshes of 1.6 mm. The resulting particles were heated at 39° C. for 4.5 h under inert atmosphere, cryo-milled with dry ice and subsequently mixed with lactose (lactose: resulting particle=100:15 w:w). The so obtained mixture was finally pressed into chewable tablets having a diameter of 16 mm, a weight of 1.15 g and containing each 60 mg orlistat, 30 mg trimyristin, 60 mg glucose and 1000 mg lactose.

The above chewable tablets were applied to human volunteers during a single meal test. Human subjects consumed a meal consisting of 130 g hamburger meat, 10 g butter and 100 g French fries (fried in peanut oil) and containing overall about 35 g fat. Stools were collected from day-1 (a day before eating the single meal) until day 5 after the test meal. The first and the last stools were employed to assess background fat excretion. Stools were stored frozen and extracted for total lipid according to Bligh and Dyer (Bligh, E. G., and Dyer, W. J., Can. J. *Biochem. Physiol.*, 37, (1959), 911). Background excretion of lipids was subtracted to obtain the amount of fat excreted due to the orlistat treatment. The excreted fat was quantified by gravimetry and expressed as percentage of the fat content of the test meal.

Example 2

100 g of trimyristin (Dynasan 114, Hüls AG) were melted at 65° C. in a suitable high shear mixer vessel. 200 g orlistat were given in the vessel and molten by mixing softly (mixture=comelt). The molten phase was mixed for 2 minutes. While stirring, 1800 g maltodextrin DE 21 (ratio comelt:maltodextrin=1:6 w:w) were added in two portions and mixed until solidification at room temperature and a flowing granulate was obtained. The granulate was sieved through meshes of 0.85 mm. Separately, 4950 g sorbitol were sieved through meshes of 0.85 mm and mixed with the co-melted granulate for 3 minutes. Additionally, the outer phase (375 g talcum and 75 g magnesium stearate) were hand sieved through meshes of 0.5 mm and mixed with the granulate for 3 minutes. The so obtained mixture was finally pressed into chewable tablets having a diameter of 20 mm, a weight of 1.5 g and containing each 40 mg orlistat, 20 mg trimyristin, 360 mg maltodextrin, 960 mg sorbitol, 75 mg talcum and 15 mg magnesium stearate.

The above chewable tablets were applied to human volunteers according to the method described in Example 1.

Example 3

1.25 g HPMC (Pharmacoat 603, Shin-Etsu Chemical Co) were dissolved in 39.5 g water at about 75° C. The solution was cooled to room temperature (25° C.) and a dispersion was obtained by adding thereto 5 g mannitol, 2.5 g sodium bicarbonate and 1 g Crospovidone. 0.75 g Kryosomes 1703H (hydrogenated lecithin, Lipoid AG) were dispersed in 7.5 g water with a homogenizer (Polytron) for 30 seconds and successively mixed with the above dispersion. The obtained aqueous system was used to make an emulsion by emulsifying, with a Polytron for 1.5 minutes at 65° C., 4.5 g of a melted oily mixture obtained by comelting 3.15 g trimyristin (Dynasan 114, Hüls AG) and 6.3 g orlistat at 65° C. This emulsion was frozen at −80° C. in a rotating 250 ml round flask in a dry ice-ethanol mixture and was then lyophilized. The lyophilisate was then milled at room temperature and 3 g thereof were mixed and sieved through meshes of 0.5 mm. 1.3 g of the mixture was pressed to a chewable tablet having a diameter of 16 mm diameter, a weight of 1.3 g and containing each 60 mg orlistat, 30 mg trimyristin, 15 mg Kryrosome, 25 mg HPMC, 20 mg Crospovidone, 100 mg mannitol, 50 mg sodium bicarbonate and 1000 mg lactose.

The above chewable tablets were applied to human volunteers according to the method described in Example 1.

Example 4

30 g orlistat and 15 g trimyristin (Dynasan 114, Hüls AG) were spread through meshes of 0.9 mm and mixed for 10 minutes. The mixture was again sieved through meshes of 0.9 mm and mixed for 10 minutes. The so obtained mixture was coarse milled (in portions) for 0.5 minutes in a dry mixer by adding a triple amount of dry ice. This cold mixture was then cryo-milled with a pin mill to get fine particles. The resulting particles were dried during 15 minutes under high vacuum and subsequently mixed with ⅔ (w/w) part of glucose. 15 g of this dry mix was mixed with 100 g lactose for 10 minutes and then sieved through meshes of 0.5 mm. The so obtained mix-milled granulate was finally pressed into chewable tablets having a diameter of 16 mm, a weight of 1.15 g and containing each 60 mg orlistat, 30 mg trimyristin, 60 mg glucose and 1000 mg lactose.

The above chewable tablets were applied to human volunteers according to the method described in Example 1.

Example 5

1.2 g orlistat and 1.8 g glucose were sieved through meshes of 0.9 mm and mixed for 2 minutes. Afterwards 4.0 g Kkryosome 1702 (soya lecithin: sucrose=1:2 w:w; Lipoid AG) were also sieved through meshes of 0.9 mm and mixed with the first mixture for 2 minutes. The combined mixture was then cryo-milled with an air-jet mill using dry ice for cooling. The resulting particles were dried for 15 minutes under high vacuum. 3.5 g of the dried particles were mixed with 10 g lactose for 15 minutes. The so obtained powder mixture was finally pressed into chewable tablets having a diameter of 16 mm, a weight of 1.35 g and containing each 60 mg orlistat, 90 mg glucose, 200 mg Kryosome and 1000 mg lactose.

The above chewable tablets were applied to human volunteers according to the method described in Example 1.

Example 6

4.24 g soyalecithin and 4.24 g orlistat were subsequently dissolved in 31.52 g glycofurol 75 (Roche). Empty hard gelatin capsules were sealed with a 25% gelatin solution in water and were allowed to dry. The sealed hard gelatin capsules were punched and subsequently filled with 565 mg of the orlistat/lecithin/glycofurol-solution. The holes were closed with the above gelatin solution and the closed capsule was allowed to dry for at least 15 minutes. Every capsule contained 60 mg orlistat, 60 mg soya lecithin and 445 mg glycofurol.

Capsules prepared in this way were applied to human volunteers according to the method described in Example 1.

Example 7

10 g of melted trimyristin (Dynasan 114, Hüls AG) were mixed with 20 g orlistat during about 30 minutes at a temperature of 57–63° C. 20 g glucose were added to the so obtained co-melt and mixed until solidification at room temperature, ground by means of a dry mixer and subsequently sieved through meshes of 1.6 mm. 48 g of resulted particles were kept at 39° C. in a closed vial under inert atmosphere for 4.5 h, cryo-milled with dry ice on a pin mill. 15 g of the resulted particles were subsequently mixed with 10 g Kryosome 1702 (Lipoid AG) and 100 g lactose for 30 minutes. The mixture was sieved through meshes of 0.5 mm and pressed into chewable tablets, having a diameter of 16 mm, a weight of 1.25 g and containing each 60 mg orlistat, 30 mg trimyristin, 60 mg glucose, 100 mg Kryosome and 1000 mg lactose.

The above chewable tablets were applied to human volunteers according to the method described in Example 1.

Example 8

0.75 g of co-melted and cryo-milled material (orlistat-trimyristin-glucose 1:2:1) from Example 7 and 0.5 g Kryosome 1702 were sieved through meshes of 0.5 mm and mixed for 10 minutes. 3.0 g sodium bicarbonate and 1.5 g tartaric acid were milled at room temperature in a laboratory blade mill, sieved through meshes of 0.5 mm and mixed for 10 minutes. 2.7 g of this effervescent mixture was added to the first mixture and mixed again for 10 minutes. 0.395 g of this mixture were filled into HPMC capsules of size 0, containing 30 mg orlistat, 15 mg trimyristin, 30 mg glucose, 50 mg Kryosome, 180 mg sodium bicarbonate and 90 mg tartaric acid.

The above capsules were applied to human volunteers according to the method described in Example 1.

Example 9

20 g orlistat and 10 g trilaurin (Dynasan 112, Hüls AG) were sieved through meshes of 0.5 mm and mixed. This mixture was cryo-milled in a pin mill together with dry ice and subsequently dried under vacuum for 15 minutes. 10 g of this mixture was blended with 15 glucose. 3g of this blend and 2 g of Kryosomes 1702 (Lipoid AG) were cryo-milled together with dry ice in a laboratory blade-mill and dried overnight in a dessicator under vacuum. 1.25 g of the resulting powder were pressed to a chewable tablet having a diameter of 16 mm, a weight of 1.25 g and containing each 60 mg orlistat, 30 mg trilaurin, 60 mg glucose, 100 mg kryosome and 1000 mg lactose.

The above chewable tablets were applied to human volunteers according to the method described in Example 1.

Example 10

16 g monolaurin (Rylo MG12, Danisco Ingredient AG) and 4 g monocaprin emulsifier TS-PHOO3 (Danisco Ingredient AG) were comelted at about 70° C., cooled to room temperature (25° C.) and thereby completely solidified. After one day the film was scraped off the wall with a spatula, coarse milled, in portions, in a dry mixer at low temperature by adding dry ice (three times the volume of the to milled material) for about half a minute and then fine cryo-milled in a pin mill and vacuum dried for 15 minutes. 15 g of this mixture and 15 g orlistat were blended. 50 g dry ice were added and the mixture is coarse milled in portions each for half a minute. After vacuum drying the resulting powder was sieved through meshes of 0.9mm and fine cryo milled in a pin mill to produce a fine orlistat-monocaprin-monolaurin (50-10-40) powdermix. 2.4 g of a comilled mixture between 2.16 g tartaric acid and 4.56 g sodiumbicarbonate was added to 5.6 g of the above powdermix and 2 g anhydrous lactose, mixed for 5 minutes and sieved through meshes of 0.5 mm and mixed again. 500 mg of the resulting powder were filled in hard gelatin capsules containing 60 mg orlistat, 48 mg monolaurin, 12 mg monocaprin, 100 mg lactose, 190 mg sodium bicarbonate and 90 mg tartaric acid.

The above capsules were applied to human volunteers according to the method cribed in Example 1.

TABLE 1

In vivo results

| Example | Orlistat dose (mg) | Excreted fat[1] | n[2] | Free oil in stool samples[3] |
| --- | --- | --- | --- | --- |
| Reference | 120 mg (Xenical ®) | 41.8 ± 11.5 | 18 | 9/18 |
| 1 | 60 mg | 48.1 ± 3.9 | 3 | 1/3 |
| 2 | 40 mg | 37.6 ± 17.1 | 5 | 0/5 |
| 3 | 60 mg | 50.2 ± 13.4 | 3 | 1/3 |
| 4 | 60 mg | 43.1 ± 15.6 | 5 | 0/5 |
| 5 | 60 mg | 64.8 ± 14.3 | 5 | 0/5 |
| 6 | 60 mg | 47.2 ± 12.0 | 5 | n.d. |
| 7 | 60 mg | 82.0 ± 5.5 | 6 | 0/6 |
| 8 | 30 mg | 40.6 ± 10.6 | 5 | 0/5 |
| 9 | 60 mg | 60.6 ± 13.3 | 5 | 2/5 |
| 10 | 60 mg | 54.2 ± 10.9 | 5 | 1/5 |

[1]excreted fat as percentage of fat intake.
[2]number of volunteers subjected to the experiments
[3]number of stool samples containing free oil/number of volunteers As shown in Table 1, the efficacy and/or potency of the compositions according to the present invention is much higher than that of conventional formulations. Compositions according to the invention containing just the half or even a quarter of the lipase inhibitor of the known composition are similarly or even much more efficacious and/or potent. For the same lipase inhibition degree, it is now possible to strongly decrease the amount of active compound in the composition, thus minimizing undesired side effects.

Table 1 shows also the number of stool samples containing free oil for each of the above compositions. Stool samples obtained after intake of compositions according to the present invention show just occasional separation of oil from the main stool mass or no separation at all. The compositions according to the present invention enable therefore to minimize or completely suppress anal leakage of oil, which is one of the most undesired side effect of the prior art compositions.

The subject invention has been described in terms of preferred embodiments. Upon reading the present specification, various alternative embodiments will become obvious to one skilled in the art. These variations are to be considered in the scope and spirit of the subject invention, which is only to be limited by the claims that follow and their equivalents.

What is claimed is:

1. A pharmaceutical composition comprising orlistat and at least one fatty acid ester of a polyol, wherein the fatty acid ester of a polyol has a melting point above body temperature and the polyol is chosen from the group consisting of sugars, sugar derivatives, and mixtures of sugars and sugar derivatives.

2. The pharmaceutical composition according to claim 1, wherein the polyol is selected from the group consisting of sucrose, glycerol, and sugar alcohols.

3. The pharmaceutical composition according to claim 2, wherein the polyol is glycerol.

4. The pharmaceutical composition according to claim 1, wherein the fatty acid ester of a polyol is a glyceride ester.

5. The pharmaceutical composition according to claim 4, wherein the glyceride moiety in the glyceride ester is chosen from the group consisting of one or more triglycerides, one or more monoglycerides, one or more phospholipids, and mixtures thereof.

6. The pharmaceutical composition according to claim 1, wherein the fatty acid moieties in the fatty acid ester of the polyol have, independently from each other, twelve or more carbon atoms, and the fatty acid ester of the polyol is saturated.

7. The pharmaceutical composition according to claim 6, wherein the fatty acid moieties in the fatty acid ester of the polyol have, independently from each other, twelve to twenty carbon atoms.

8. The pharmaceutical composition according to claim 4, wherein the polyol is a triglyceride chosen from the group consisting of trilaurin, trimyristin, tripalmitin, tristearin, and mixtures thereof.

9. The pharmaceutical composition according to claim 8, wherein the triglyceride is trimyristin, trilaurin, or a mixture thereof.

10. A pharmaceutical composition comprising orlistat and at least one ester of a monoglyceride chosen from the group consisting of monocaprin, monolaurin, monomyristin, monopalmitin, and mixtures thereof, wherein the ester has a melting point above body temperature.

11. A pharmaceutical composition comprising orlistat and at least one ester of a phospholipid that is a lecithin, wherein the ester has a melting point above body temperature.

12. The pharmaceutical composition according to claim 11, wherein the lecithin is a non-, partially or fully hydrogenated lecithin, or a mixture thereof.

13. The pharmaceutical composition according to claim 11, wherein the lecithin is selected from the group consisting of natural lecithin, syntlletic lecithin, soya lecithin, egg lecithin, synthetic dipalmitoyllecithin, partially or fully hydrogenated lecithin, and mixtures thereof.

14. The pharmaceutical composition according to claim 1, wherein the at least one fatty acid ester of a polyol is present in an amount varying between 0.5% and 90% of the total weight of the composition.

15. The pharmaceutical composition according to claim 1 further comprising at least one pharmaceutically acceptable excipient.

16. The pharmaceutical composition according to claim 15, wherein the excipient is selected from the group consisting of carbohydrates, starch, starch derivatives, maltodextrines, cellulose, cellulose derivatives, sugars, fillers, disintegrants, effervescents, antioxidants, anionic surfactants, nonionic surfactants, and mixtures thereof.

17. The pharmaceutical composition according to claim 16, wherein the excipient is a surfactant selected from the group consisting of sodium dodecylsulfate, fatty acid salts, polyoxyethylene alkyl esters and polyoxyethylene alkyl ethers, and mixtures thereof.

18. The pharmaceutical composition according to claim 15, wherein the at least one excipient is selected from the group consisting of glucose, lactose, sorbitol, maltodextrin, talcum, magnesium stearate, mannitol, sodium bicarbonate, Crospovidone, glycofurol, tartaric acid, and mixtures thereof.

19. The pharmaceutical composition according to claim 1, wherein the orlistat is present in an amount between 1% and 50% of the total weight of the composition.

20. The pharmaceutical composition according to claim 19, wherein the orelistat is present in an amount between 5% and 30% of the total weight of the composition.

21. The pharmaceutical composition according to claim 19, which comprises:
   a) orlistat is forms from 1% to 50% of the total weight of the composition; and
   b) at least one fatty acid ester of a polyol that forms from 0.5% to 90% of the total weight of the composition.

22. The pharmaceutical composition according to claim 21 further comprising one or more pharmaceutically acceptable excipient(s).

* * * * *

UNITED STATES PATENT AND TRADEMARK OFFICE
CERTIFICATE OF CORRECTION

PATENT NO. : 6,703,369 B1
DATED : March 9, 2004
INVENTOR(S) : Passchier Christiaan de Smidt et al.

It is certified that error appears in the above-identified patent and that said Letters Patent is hereby corrected as shown below:

Title page,
Item [73], Assignee, delete "Hoffman-La Roche Inc., Nutley, NJ (US)" and insert
-- Hoffmann-La Roche Inc., Nutley, NJ (US) --.

Column 10,
Line 9, delete "The pharmaceutical composition according to claim 11, wherein the lecithin is selected from the group consisting of natural lecithin, syntlIetic lecithin, soya lecithin, egg lecithin, synthetic dipalmitoyllecithin, partially or fully hydrogenated lecithin, and mixtures thereof." and insert -- The pharmaceutical composition according to claim 11, wherein the lecithin is selected from the group consisting of natural lecithin, synthetic lecithin, soya lecithin, egg lecithin, synthetic dipalmitinlecithin, partially or fully hydrogenated lecithin, and mixtures thereof. --
Line 32, delete "The pharmaceutical composition according to claim 15, wherein the at least one excipient is selected from the group consisting of glucose, lactose, sorbitol, maltodextrin, talcum, magnesium stearate, mannitol, sodium bicarbonate, Crospovidone, glucofurol, tartaric acid, and mixtures thereof." and insert -- The pharmaceutical composition according to claim 15, wherein the at least one excipient is selected from the group consisting of glucose, lactose, sorbitol, maltodextrin, talcum, magnesium stearate, mannitol, sodium bicarbonate, crospovidone, glucofurol, tartaric acid, and mixtures thereof. --
Line 41, delete "The pharmaceutical composition according to claim 19, wherein the orelistat is present in an amount between 5% and 30% of the total weight of the composition," and insert -- The pharmaceutical composition according to claim 19, wherein the orlistat is present in an amount between 5% and 30% of the total weight of the composition. --

Signed and Sealed this

Fifth Day of October, 2004

JON W. DUDAS
*Director of the United States Patent and Trademark Office*